US012749159B2

(12) United States Patent
Huber et al.

(10) Patent No.: US 12,749,159 B2
(45) Date of Patent: Sep. 29, 2026

(54) GENERALIZABLE IMAGE-BASED TRAINING FRAMEWORK FOR ARTIFICIAL INTELLIGENCE-BASED NOISE AND ARTIFACT REDUCTION IN MEDICAL IMAGES

(71) Applicant: Mayo Foundation for Medical Education and Research, Rochester, MN (US)

(72) Inventors: Nathan R. Huber, Saint Peter, MN (US); Shuai Leng, Rochester, MN (US); Andrew D. Missert, Rochester, MN (US); Lifeng Yu, Byron, MN (US); Cynthia H. McCollough, Byron, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 364 days.

(21) Appl. No.: 18/546,374

(22) PCT Filed: Feb. 14, 2022

(86) PCT No.: PCT/US2022/016337

§ 371 (c)(1),
(2) Date: Aug. 14, 2023

(87) PCT Pub. No.: WO2022/174152

PCT Pub. Date: Aug. 18, 2022

(65) Prior Publication Data

US 2024/0135502 A1 Apr. 25, 2024
US 2024/0233091 A9 Jul. 11, 2024

Related U.S. Application Data

(60) Provisional application No. 63/148,875, filed on Feb. 12, 2021.

(51) Int. Cl.
*G06T 5/60* (2024.01)
*G06T 5/50* (2006.01)
(Continued)

(52) U.S. Cl.
CPC .................. *G06T 5/60* (2024.01); *G06T 5/50* (2013.01); *G06T 5/70* (2024.01); *G16H 30/40* (2018.01);
(Continued)

(58) Field of Classification Search
None
See application file for complete search history.

(56) References Cited

U.S. PATENT DOCUMENTS 10,635,943 B1 4/2020 Lebel et al.
10,692,189 B2 6/2020 Mentl et al.
(Continued)

FOREIGN PATENT DOCUMENTS

EP 3633601 A1 4/2020
WO 2019240257 A1 12/2019

OTHER PUBLICATIONS

International Search Report of related PCT/US2022/016337, mailed on Jul. 14, 2022, 6 pages.
(Continued)

*Primary Examiner* — Jiangeng Sun
(74) *Attorney, Agent, or Firm* — Quarles & Brady LLP

(57) ABSTRACT

A neural network is trained and implemented to simultaneously remove noise and artifacts from medical images using a Generalized noise and Artifact Reduction Network ("GARNET") method for training a convolutional neural network ("CNN") or other suitable neural network or machine learning algorithm. Noise and artifact realizations from phantom images are used to synthetically corrupt images for training. Corrupted and uncorrupted image pairs
(Continued)

are used for training GARNET. Following the training phase, GARNET can be used to improve image quality of routine medical images by way of noise and artifact reduction.

12 Claims, 4 Drawing Sheets

(51) Int. Cl.
*G06T 5/70* (2024.01)
*G16H 30/40* (2018.01)

(52) U.S. Cl.
CPC ............... *G06T 2207/10081* (2013.01); *G06T 2207/10088* (2013.01); *G06T 2207/10116* (2013.01); *G06T 2207/10132* (2013.01); *G06T 2207/20081* (2013.01); *G06T 2207/20084* (2013.01); *G06T 2207/20224* (2013.01); *G06T 2207/30004* (2013.01)

(56) References Cited

U.S. PATENT DOCUMENTS

| | | | | |
|---|---|---|---|---|
| 2007/0076841 | A1* | 4/2007 | Varadharajan | A61B 6/032 378/10 |
| 2018/0018757 | A1* | 1/2018 | Suzuki | A61B 6/5205 |
| 2018/0268526 | A1* | 9/2018 | Mentl | G06T 5/60 |
| 2019/0005686 | A1* | 1/2019 | Liu | G16H 40/63 |
| 2021/0104313 | A1 | 4/2021 | Mizobe et al. | |
| 2022/0107378 | A1* | 4/2022 | Dey | G06N 3/09 |
| 2023/0342928 | A1* | 10/2023 | Do | G06T 7/0012 |

OTHER PUBLICATIONS

Written Opinion of related PCT/US2022/016337, mailed on Jul. 14, 2022, 14 pages.
Borsdorf, Anja, et al. "Wavelet based noise reduction in CT-images using correlation analysis." IEEE transactions on medical imaging 27.12 (2008): 1-20.
Chen, H., Zhang, Y., Kalra, M. K., Lin, F., Chen, Y., Liao, P., . . . & Wang, G. (2017). Low-dose CT with a residual encoder-decoder convolutional neural network. IEEE transactions on medical imaging, 36(12), 2524-2535.
Chen, Y., et al. (2012). Thoracic low-dose CT image processing using an artifact suppressed large-scale nonlocal means. Physics in medicine & biology, 57(9), 2667.
Hara, A. K., Paden, R. G., Silva, A. C., Kujak, J. L., Lawder, H. J., & Pavlicek, W. (2009). Iterative reconstruction technique for reducing body radiation dose at CT: feasibility study. American Journal of Roentgenology, 193(3), 764-771.
Huber, Nathan R., et al. "Phantom-based training framework for convolutional neural network CT noise reduction." Medical physics 50.2 (2023): 821-830.
Huber, Nathan R., et al. "Random search as a neural network optimization strategy for Convolutional-Neural-Network (CNN)-based noise reduction in CT." Medical Imaging 2021: Image Processing. vol. 11596; 1-10. SPIE, (2021).
Jain, V., & Seung, S. (2008). Natural image denoising with convolutional networks. Advances in neural information processing systems, 21: 1-8.
Kang, E., Min, J., & Ye, J. C. (2017). A deep convolutional neural network using directional wavelets for low-dose X-ray CT reconstruction. Medical physics, 44(10), e360-e375.
Li, Zhoubo, et al. "Adaptive nonlocal means filtering based on local noise level for CT denoising." Medical physics 41.1 (2014): 011908-1-011908-16.
Mao, X., Shen, C., & Yang, Y. B. (2016). Image restoration using very deep convolutional encoder-decoder networks with symmetric skip connections. Advances in neural information processing systems, 29: 1-9.
McCollough, C. H., Bartley, A. C., Carter, R. E., Chen, B., Drees, T. A., Edwards, P., . . . & Fletcher, J. G. (2017). Low-dose CT for the detection and classification of metastatic liver lesions: results of the 2016 low dose CT grand challenge. Medical physics, 44(10), e339-e352.
Rabbani, Hossein, Reza Nezafat, and Saeed Gazor. "Wavelet-domain medical image denoising using bivariate laplacian mixture model." IEEE transactions on biomedical engineering 56.12 (2009): 2826-2837.
Wang, Jing, et al. "Penalized weighted least-squares approach to sinogram noise reduction and image reconstruction for low-dose X-ray computed tomography." IEEE transactions on medical imaging 25.10 (2006): 1272-1283.
Xie, J., Xu, L., & Chen, E. (2012). Image denoising and inpainting with deep neural networks. Advances in neural information processing systems, 25 (pp. 1-9).
Xie, S., Girshick, R., Dollár, P., Tu, Z., & He, K. (2017). Aggregated residual transformations for deep neural networks. In Proceedings of the IEEE conference on computer vision and pattern recognition (pp. 1492-1500).
Yin, X., Zhao, Q., Liu, J., Yang, W., Yang, J., Quan, G., . . . & Coatrieux, J. L. (2019). Domain progressive 3D residual convolution network to improve low-dose CT imaging. IEEE transactions on medical imaging, 38(12), 2903-2913.
Huber, Nathan, et al. "Clinical evaluation of a phantom-based deep convolutional neural network for whole-body-low-dose and ultra-low-dose CT skeletal surveys." Skeletal Radiology 51.1 (2022): 145-151.
Missert, Andrew D., et al. "Simulation of CT images reconstructed with different kernels using a convolutional neural network and its implications for efficient CT workflow." Medical Imaging 2019: Physics of Medical Imaging. vol. 10948; 1-6. SPIE, 2019.
Shan, Hongming, et al. "Competitive performance of a modularized deep neural network compared to commercial algorithms for low-dose CT image reconstruction." Nature Machine Intelligence 1.6 (2019): 269-276.

* cited by examiner

GENERALIZABLE IMAGE-BASED TRAINING FRAMEWORK FOR ARTIFICIAL INTELLIGENCE-BASED NOISE AND ARTIFACT REDUCTION IN MEDICAL IMAGES

STATEMENT REGARDING FEDERALLY SPONSORED RESEARCH

This invention was made with government support under EB028591, EB028590, and EB016966 awarded by the National Institutes of Health. The government has certain rights in the invention.

BACKGROUND

Within computed tomography ("CT"), as well as other medical imaging modalities, there is significant interest in reduction of noise and artifacts, which are commonly seen in routine exams. Medical image noise and artifacts impede a radiologist's ability to make an accurate diagnosis.

Deep learning-based image denoising is being actively explored for improving image quality. However, there is a lack of methods to simultaneously reduce image noise and remove artifacts. Deep learning denoising algorithms often utilize multiple high-noise and low-noise realizations for training the network to differentiate anatomical signal from image noise, consequently, to reduce image noise while maintaining anatomical structures. These training images could in theory be obtained from separated scans with low-dose and routine-dose. However, they are difficult to obtain in practice due to radiation dose considerations. Even if scans at different dose levels were available, there is no guarantee of perfect spatial matching due to variations of scanning position and intrinsic and adverse motion of the human body.

Deep learning-based image denoising is commonly implemented using training data generated by use of projection noise insertion. Random Poisson noise is added to CT projection data to mimic the quantum fluctuations associated with a low-dose exam. Following CT reconstruction, the simulated low-dose exam contains image noise that accurately mimics noise observed in low-dose acquisitions. Deep-learning algorithms are then trained using the projection-based noise insertion image as an input and the corresponding routine dose image as the ground truth.

There are several problems that result from using projection noise insertion. As one drawback, the projection noise insertion training method requires access to CT projection data. There are at least two challenges associated with this requirement. In most instances, projection data from clinical CT scans cannot be accessed by entities independent of the scanner vendor. Furthermore, projection data are not routinely saved, therefore retrospective projection data are not generally available (compared to image data, which are commonly retrospectively accessible). This limited access to projection data is a barrier for many considering the implementation of deep-learning noise reduction methods.

Another drawback to existing deep learning noise and artifact reduction techniques is artifact correlations within projection noise inserted images and original routine dose images. As a general tenet of deep-learning artifact correction methods, the ground truth should not contain the artifact to be removed. In the case of projection noise insertion, streaks resulting from photon starved regions often align within the simulated low dose image and the routine dose ground truth. In these instances, it is difficult to train the network to completely remove the artifact whenever there is artifact correlation between the input and ground truth image.

A calibration process is also required for the projection noise insertion algorithms, which is scanner-model dependent. Therefore, considerable amount of effort is needed for calibration of noise insertion for each scanner model. Each noise realization in the training dataset must be independently inserted into the projection data and reconstructed when using projection noise insertion methods. This process requires significant computational burden when considering the size of datasets used for training deep-learning denoising algorithms. To retrain the deep learning model on different patients would require repeating the noise insertion and reconstruction process.

In addition to image noise, the CT acquisition and reconstruction process results in streak artifacts. State-of-the-art CNN denoising algorithms using projection noise insertion have not been capable of efficient removal of streak artifact.

SUMMARY OF THE DISCLOSURE

The present disclosure addresses the aforementioned drawbacks by providing a method for reducing noise and artifacts in previously reconstructed medical images. Patient medical image data are accessed with a computer system, where the patient medical image data include one or more medical images acquired with a medical imaging system and depicting a patient. A trained neural network is also accessed with the computer system. The trained neural network has been trained on training data that include noise-augmented image data generated by combining image data with noise-only data obtained with the medical imaging system. The patient medical image data are input to the trained neural network using the computer system, generating output as uncorrupted patient medical image data. The uncorrupted patient medical image data comprise one or more medical images depicting the patient and having reduced noise and artifacts relative to the patient medical image data.

It is another aspect of the present disclosure to provide a method for training a neural network to reduce noise and artifacts in medical images acquired with a medical imaging system. Image data acquired with the medical imaging system are accessed with a computer system, where the image data include noise and artifacts attributable to the medical imaging system. Uncorrupted image data are also accessed with the computer system. Training data are generated with the computer system by combining the noise and artifact containing image data with the uncorrupted image data, where the training data are representative of the uncorrupted image data being augmented with the noise and artifacts present in the image data and attributable to the medical imaging system. A neural network is trained on the training data using the computer system, generating output as trained neural network parameters. The neural network is trained in order to learn to differentiate noise and signal features specific to medical images acquired with the medical imaging system. The trained neural network parameters are then stored as the trained neural network.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
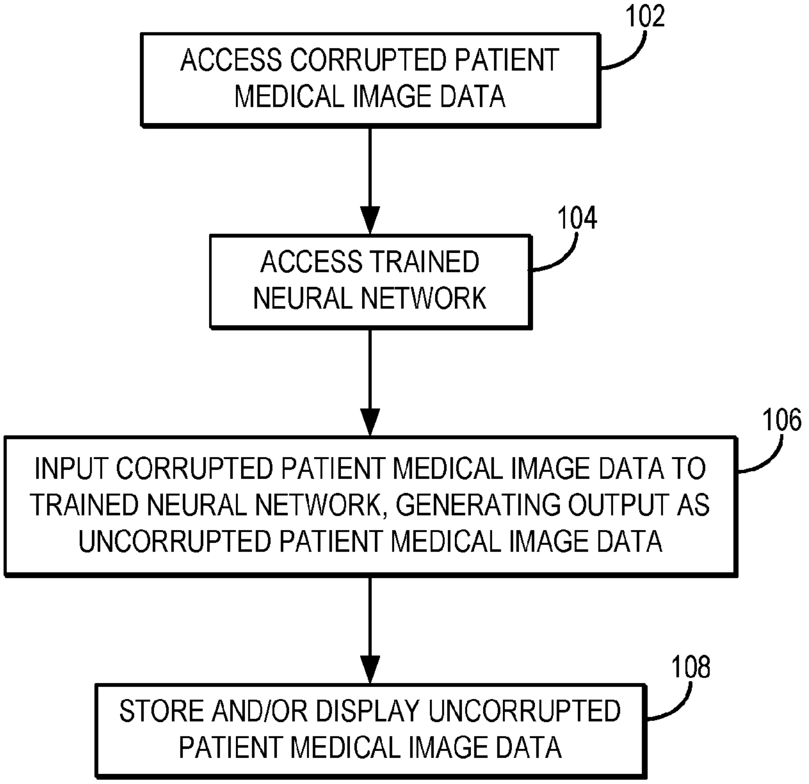
FIG. 1 is a flowchart setting forth the steps of an example method for reducing noise and artifacts in patient medical images using a neural network trained on phantom-augmented image data.

Described here are systems and methods for training and implementing a neural network, a machine learning algorithm or model, or other suitable artificial intelligence ("AI") model, to simultaneously remove noise and artifacts from medical images using a Generalizable noise and Artifact Reduction Network ("GARNET") method, for training a convolutional neural network ("CNN") or other suitable neural network, machine learning algorithm or model, or AI model. The systems and methods described in the present disclosure are applicable to a number of different medical imaging modalities, including magnetic resonance imaging ("MRI"); x-ray imaging, including computed tomography ("CT"), fluoroscopy, and so on; ultrasound; and optical imaging modalities, including photography, pathology imaging, microscopy, optical coherence tomography, and so on.

Noise-only images are generated from reconstructed images that have been obtained using a specific medical imaging system. The noise-only images include the noise and artifact image content separated from the signal components of the original image. Noise-only images can be obtained from phantom images or patient data.

Phantom or patient data are acquired and reconstructed to provide noise and artifact realizations for a specific medical imaging system, which may include a particular imaging system, or a particular imaging system model. For example, the image data may be obtained for a particular CT scanner model. Noise and artifact realizations from the phantom or patient images are used to synthetically corrupt patient medical images. Although noise-only images used in training can be generated from phantom or patient images, in many instances they can be referred to as phantom images or phantom noise images in the present disclosure. The synthetically corrupted patient images are used as training input and the uncorrupted patient images are used as a training target for GARNET-CNN.

Following the training phase, GARNET-CNN can be used to improve image quality of routine medical images by way of noise and artifact reduction. Examples of the systems and methods will be described in the present disclosure with respect to CT imaging; however, as noted above the GARNET-CNN is applicable to other medical imaging modalities. The GARNET-CNN systems and methods described in the present disclosure represent a widely accessible and efficient training method in CNN noise and artifact reduction because the noise used for training is extracted from the image domain.

In general, a trained neural network, or other machine learning algorithm, is used to simultaneously remove noise and artifacts simultaneously. Patient images are merged with noise-only images of a phantom, or patient, taken with the imaging system of interest. A neural network, or other machine learning algorithm, is then trained to separate the noise and artifacts from the original patient images. Because the phantom and/or patient images used for augmentation contain scanner-specific noise and artifacts, the neural network, other machine learning algorithm, or other AI model learns to output patient images with significantly reduced noise and artifacts, and with an image quality similar to, or even better than, what is obtained with routine imaging protocols (e.g., high dose scans in CT, long scan times in MRI).

Advantageously, the systems and methods described in the present disclosure can be implemented completely within the image domain, thereby making data access easier. Furthermore, it is an advantage that the methods are computationally efficient, can remove and/or reduce noise and artifacts simultaneously, and can be fine-tuned for a specific imaging system, or even a specific imaging system/patient combination.

Medical image noise and artifacts impede a radiologist's ability to make an accurate diagnosis. Advantageously, the systems and method described in the present disclosure provide a more efficient and effective training strategy for image-based CNN noise and artifact reduction.

The GARNET-CNN training technique described in present disclosure can be efficiently implemented and is extremely effective at noise and artifact removal when compared with related technologies. The efficiency of implementation is a result of making this training method implement data collected entirely within the image domain. In one implementation, the denoising algorithm can be calibrated for a specific imaging system of interest using a single set of phantom acquisitions and a representative set of patient images from the imaging system. In another implementation, the denoising algorithm can be calibrated using noise extracted from patient scans previously acquired by the same imaging system. The effectiveness of implementation results from the ability of the training technique to learn to differentiate noise and signal features specific to medical images. After training the network, algorithm, or model, it can be applied to routine clinical images to significantly reduce image noise and artifacts that may impede accurate diagnosis.

This invention has multiple advantages over the current noise insertion CNN denoising methods. As one advantage, no access to CT projection data, or other raw medical image data (e.g., k-space data acquired with an MRI system), is required. Because noise realizations are extracted from previously reconstructed images, the GARNET methods can be implemented completely within the image domain. This enables implementation of GARNET-CNN independent of the medical imaging system vendor. This results in at least two advantages of GARNET-CNN. Entities independent of the imaging system vendor can implement GARNET-CNN, unlike projection noise insertion CNN training methods. Additionally or alternatively, GARNET-CNN can be applied retrospectively to datasets in which the projection data (or other raw medical image data, such as k-space data) is not available. Rather, a phantom calibration scan on the imaging system can be used to generate these datasets.

As another advantage, no artifact correlations exist between the noise and artifact images and the uncorrupted medical image. When implemented using phantom data, noise and artifact images are generated completely independently of the patient data, and thus there are no correlations between the artifacts. When using patient data to obtain the noise and artifact images, the noise and artifact images are either obtained from a different patient or are reinserted into the same patient with spatial decoupling to insure there are no correlations between the artifacts.

The systems and methods described in the present disclosure also provide increased computational efficiency over projection noise injection based methods. For instance, phantom noise realizations are reconstructed independent of medical image realizations. Considering that any medical image and any phantom artifact realization can be added together to form the corrupted image input, the number of permutations possible for use as training data is extensive. Additionally, a GARNET-CNN can be readily retrained with a different patient dataset since the artifact realizations can be reused.

In some implementations, a GARNET-CNN can be optimized for a specific imaging application, whether a standard or non-standard imaging application. Other noise reduction techniques (e.g., iterative reconstruction, deep learning reconstruction) have been implemented such that they broadly generalize over many applications. This broad generalization makes them unable to optimally perform for individual applications that fall outside standard imaging protocols. The GARNET-CNN can be optimized for non-standard imaging protocols, such as renal stone CT and breast microcalcification CT.

In still other implementations, a GARNET-CNN can be used to offset the elevated noise level associated with image reconstruction of sharper and thinner images relative to standard reconstruction protocols. Traditionally, image reconstruction of sharper and thinner images results in elevated noise levels. In our implementation, we reconstruct sharper and thinner images than is standard in clinical reconstruction protocols and then apply GARNET-CNN to reduce noise level. This implementation results in improved spatial resolution while maintaining low noise level. Advantageously, processing high spatial resolutions images in this manner can improve imaging in clinical applications such as chest CT, musculoskeletal CT, head CT angiography, and the like.

Referring now to FIG. 1, a flowchart is illustrated as setting forth the steps of an example method for denoising and/or reducing artifacts in medical images of a patient by implementing a generalizable noise and artifact reduction network (GARNET). For simplicity, the method is described with respect to the training and implementation of a convolutional neural network. It will be appreciated, however, that other types of neural networks can also be trained and implemented, as can other machine learning algorithms, machine learning models, or AI models. Additionally, the technique is described for CT imaging; however, as described above it can be readily implemented for other medical imaging modalities. The technique is described for a specific residual CNN; however, the method can also be implemented using other neural network configurations.

The method includes accessing patient medical image data with a computer system, as indicated at step 102. Accessing the patient medical image data may include retrieving such data from a memory or other suitable data storage device or medium. Alternatively, accessing the patient medical image data may include acquiring such data with a medical imaging system and transferring or otherwise communicating the data to the computer system, which may be a part of the medical imaging system.

In general, the patient medical image data includes medical images having noise and/or artifacts. As such, the patient medical image data may also be referred to as corrupted patient medical image data. As noted above, in some instances the medical image data can include high spatial resolution images. For example, the high spatial resolution images can include sharp images, thin images, combinations thereof, or the like. In these instances, the GARNET-CNN can be used to manage the noise penalty associated with the increased spatial resolution.

A trained neural network (or other suitable machine learning algorithm) is then accessed with the computer system, as indicated at step 104. Accessing the trained neural network may include accessing network parameters (e.g., weights, biases, or both) that have been optimized or otherwise estimated by training the neural network on training data. In some instances, retrieving the neural network can also include retrieving, constructing, or otherwise accessing the particular neural network architecture to be implemented. For instance, data pertaining to the layers in the neural network architecture (e.g., number of layers, type of layers, ordering of layers, connections between layers, hyperparameters for layers) may be retrieved, selected, constructed, or otherwise accessed.

In general, the neural network is trained, or has been trained, on training data in order to remove noise and artifacts that are naturally generated in the patient medical images. As described in more detail below, one implementation of the training data include phantom-based artifact augmented images. Additionally or alternatively, the augmented noise can be extracted from previously acquired patient images, whether from the same patient or a different patient.

The patient medical image data are then input to the one or more trained neural networks, generating output as improved medical image data, as indicated at step 106. The improved medical image data may also be referred to as uncorrupted patient medical image data. For example, the improved medical image data may include medical images of the patient that have been denoised, or in which noise has otherwise be reduced relative to the corrupted patient medical image data. Additionally or alternatively, the improved medical image data may include medical images in which artifacts have been reduced relative to the corrupted patient medical image data. Advantageously, using the systems and methods described in the present disclosure the improved medical image data can include medical images in which both noise and artifacts have been removed or otherwise reduced relative to the corrupted patient medical image data.

The improved medical image data generated by inputting the patient medical image data to the trained neural network (s) can then be displayed to a user, stored for later use or further processing, or both, as indicated at step 108.

Figure 2:
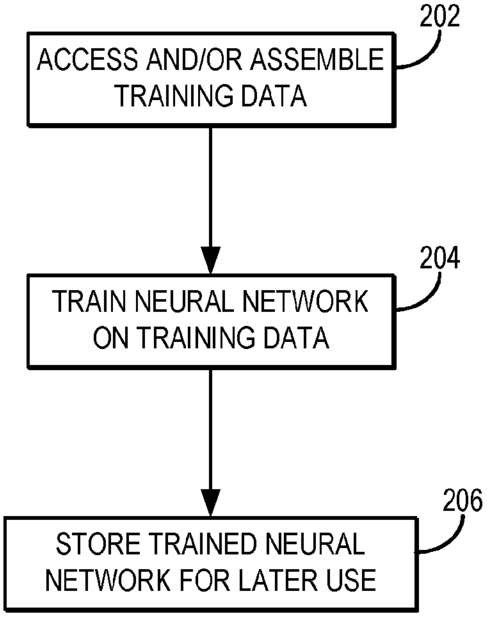
FIG. 2 is a flowchart setting forth the steps of an example method for training a neural network to differentiate noise and artifacts attributable to a medical imaging system using phantom-augmented image data.

Referring now to FIG. 2, a flowchart is illustrated as setting forth the steps of an example method for training one or more neural networks (or other suitable machine learning algorithms) on training data, such that the one or more neural networks are trained to receive input as noise and/or artifact corrupted patient medical image data in order to generate output as uncorrupted patient medical image data, in which noise and artifacts have been removed or otherwise reduced relative to the corrupted patient medical image data.

In general, the neural network(s) can implement any number of different neural network architectures. For instance, the neural network(s) could implement a convolutional neural network, a residual neural network, or the like. Alternatively, the neural network(s) could be replaced with other suitable machine learning algorithms, such as those based on supervised learning, unsupervised learning, deep learning, ensemble learning, and so on.

The method includes accessing and/or assembling training data with a computer system, as indicated at step 202. Accessing the training data may include retrieving such data from a memory or other suitable data storage device or medium. Alternatively, accessing the training data may include acquiring such data with a medical imaging system and transferring or otherwise communicating the data to the computer system, which may be a part of the medical imaging system.

In general, the training data include augmented image data that have been generated based on medical images generated using the particular medical imaging system for which the neural network will be trained. For instance, the training data can include noise-augmented image data that includes phantom-based augmented image data generated by combining phantom images acquired with the medical imaging system and subject medical images acquired with the medical image system. Additionally or alternatively, the noise-based augmented image data generated by combining phantom images acquired with the medical imaging system and natural images, such as images from an image database such as the ImageNet database. Additionally or alternatively, the augmented image data can include noise and artifacts extracted from a patient exam and combined with subject medical images acquired with the medical image system. In these instances, the augmented image data can include noise-augmented image data, artifact-augmented image data, or both. For example, the augmented image data can be augmented with noise alone, with artifacts alone, or with both noise and artifacts. As still another example, the augmented image data can include noise and artifacts extracted from a patient exam and combined with natural images, such as images from an image database such as the ImageNet database. In these instances, the augmented image data can include noise-augmented image data, artifact-augmented image data, or both. For example, the augmented image data can be augmented with noise alone, with artifacts alone, or with both noise and artifacts. As yet another example, the augmented image data can include noise-augmented image data that include noise injected using a filtered backprojection ("FBP") image reconstruction.

In some embodiments, accessing the training data includes accessing already generated training data. In some other embodiments, accessing the training data can include accessing phantom image data and subject medical image data and/or natural image data, generating the training data from the phantom image data and subject medical image data and/or natural image data, and storing the resulting image-based noise augmented image data as the training data.

Figure 3:
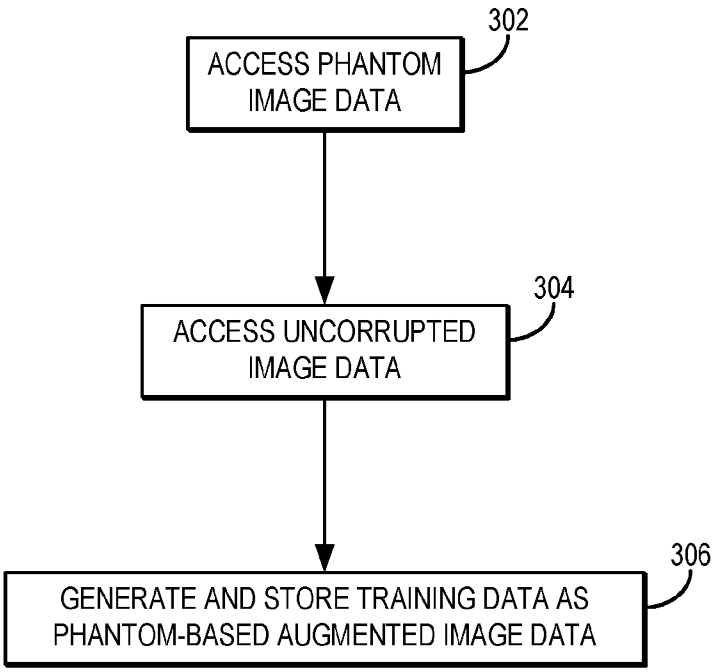
FIG. 3 is a flowchart setting forth the steps of an example method for generating phantom-augmented image data by combining phantom image data acquired with a medical imaging system and uncorrupted image data.

As an example, and referring now to FIG. 3, a flowchart is illustrated as setting forth the steps of an example method for generating training data as noise-augmented image data.

The method includes accessing image data, as indicated at step 302. Accessing the image data may include retrieving such data from a memory or other suitable data storage device or medium. Alternatively, accessing the image data may include acquiring such data with a medical imaging system and transferring or otherwise communicating the data to the computer system, which may be a part of the medical imaging system. In some examples, the image data are acquired from a phantom, and thus can be referred to as phantom image data. In other examples, the image data can be acquired from a subject or patient, which may be the same subject or patient whose images will be later obtained for noise and artifact reduction, or a different subject or patient. In these instances, the image data may also be referred to as patient image data.

The method also includes accessing uncorrupted image data, as indicated at step 304. Accessing the uncorrupted image data may include retrieving such data from a memory or other suitable data storage device or medium. Alternatively, accessing the uncorrupted image data may include acquiring such data with the same medical imaging system used to acquire the phantom image data and transferring or otherwise communicating the data to the computer system, which may be a part of the medical imaging system. The uncorrupted image data may be subject medical image data containing medical images of a subject, or natural image data containing images from a database, such as an ImageNet database. When the neural network or other AI model is trained on training data that includes natural images, transfer learning can be used to apply the neural network to patient medical images.

Noise-augmented image data are then generated by combining the image data and the uncorrupted image data, as indicated at step 306. As an example, the uncorrupted image data can be cropped into many small image patches (e.g., 64×64 voxels), which make up the image realizations used for training. Artifact and noise realizations can be obtained from the image data, which can contain multiple images of different regions. An artifact realization can be defined when the noise texture and other image artifacts are separated from the signal component of the image(s) in the image data. As one non-limiting example, the noise and artifacts can be extracted by subtracting two independent images acquired of the same imaged region. These noise and artifact realizations can be cropped into many small image patches and make up the second dataset.

For each training example, a random image realization and a random artifact realization can be selected from their respective datasets and combined. As one non-limiting example, the random image realization and random artifact realization can be combined by adding them together; however, it will be appreciated that alternative operations for combining these images can also be used. Adding the image and artifact realizations degrades the original image quality. For instance, the image quality is degraded in that there is increased presentation of artifacts as well as reduced signal-to-noise ratio. The noise-augmented image can also be referred to as a corrupted training image. The corresponding ground truth target for this training example is the original medical image realization, which may be referred to as an uncorrupted training image.

The operation of randomly combining image and artifact realizations can be performed multiple times to generate a batch of training data. With each batch or training epoch of the GARNET, new training examples can be generated by repeating the process of randomly adding image and artifact realizations.

Referring again to FIG. 2, a neural network is tasked to remove the noise and artifacts from the corrupted image(s) in the training data. One or more neural networks (or other suitable machine learning algorithms) are trained on the training data, as indicated at step 204. In general, the neural network can be trained by optimizing network parameters (e.g., weights, biases, or both) based on minimizing a loss function. As one non-limiting example, the loss function may be a mean squared error loss function.

Training a neural network may include initializing the neural network, such as by computing, estimating, or otherwise selecting initial network parameters (e.g., weights, biases, or both). Training data can then be input to the initialized neural network, generating output as uncorrupted image data. The quality of the uncorrupted can then be evaluated, such as by passing the uncorrupted image data to the loss function to compute an error. The current neural network can then be updated based on the calculated error (e.g., using backpropagation methods based on the calculated error). For instance, the current neural network can be updated by updating the network parameters (e.g., weights, biases, or both) in order to minimize the loss according to the loss function. When the error has been minimized (e.g., by determining whether an error threshold or other stopping criterion has been satisfied), the current neural network and its associated network parameters represent the trained neural network.

The one or more trained neural networks are then stored for later use, as indicated at step 206. Storing the neural network(s) may include storing network parameters (e.g., weights, biases, or both), which have been computed or otherwise estimated by training the neural network(s) on the training data. Storing the trained neural network(s) may also include storing the particular neural network architecture to be implemented. For instance, data pertaining to the layers in the neural network architecture (e.g., number of layers, type of layers, ordering of layers, connections between layers, hyperparameters for layers) may be stored.

Figure 4:
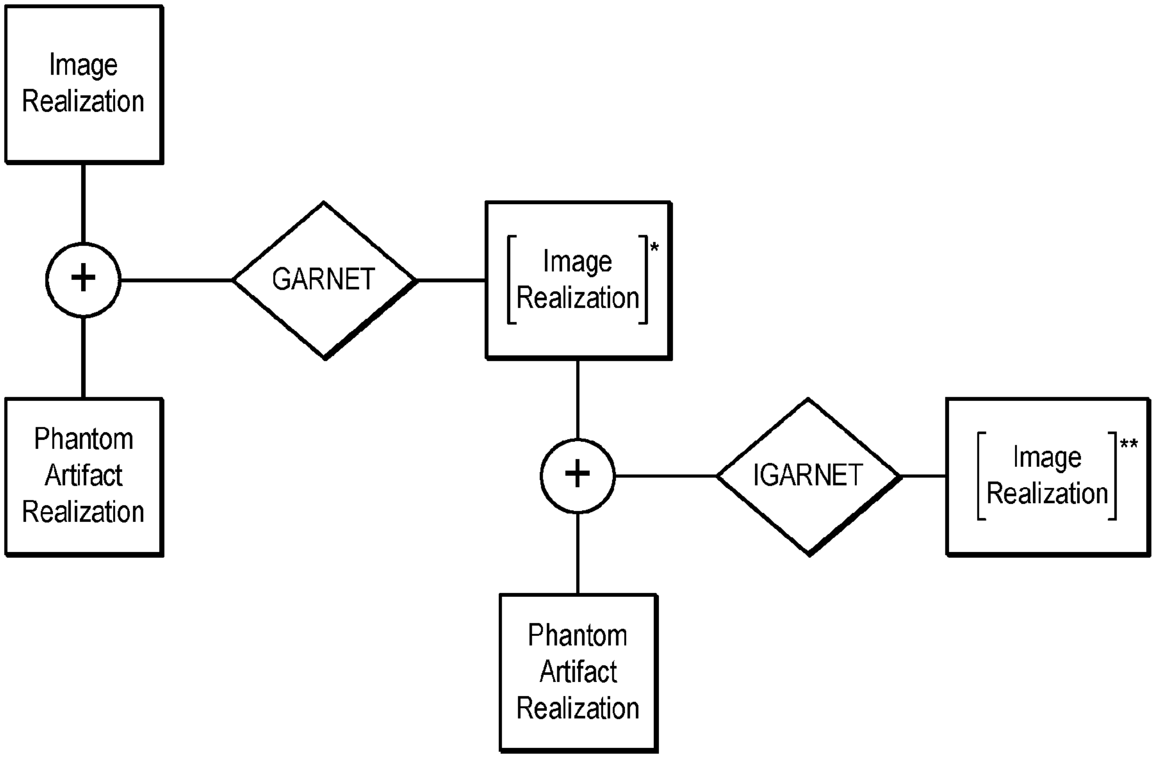
FIG. 4 illustrates an iterative training process that can be used to train a neural network in some embodiment described in the present disclosure.

Additionally or alternatively, training of the neural network can be performed in an iterative manner. An example of an iterative training process is illustrated in FIG. 4. In this variation of the GARNET training method, the first network is trained using artifact-corrupted images as the input and the uncorrupted image as the target, similar to the training process described above. Next, all of the training image patches are fed through the CNN that was just trained. This process removes some of the natural noise and artifacts observed within the image patches used for training. The result of applying this CNN to the training dataset can be referred to as [Image Realization]*. Artifact and noise augmentation is then repeated for [Image Realization]*. The training input of IGARNET is the artifact and noise augmented [Image Realization]* and the training target is the uncorrupted [Image Realization]**.

In contrast to ensemble CNN frameworks, only the most recently trained network (IGARNET) should be applied to the test dataset. The benefit of this iterative training strategy is use of increasingly noise and artifact-free ground truth. This process can be performed for multiple iterations for the network to perform increasingly thorough noise and artifact reduction. It is contemplated that this iterative training method can be used as a way to tune the extent of the networks noise and artifact reduction for specific tasks or human observer preference.

As described above, in some implementations, the training data may include noise-augmented natural images. In these instances, the training data are generated by combining artifact and noise realization with natural (optical) image realizations rather than subject medical image realizations. The neural network is then trained for noise reduction of natural images and then applied to patient medical image data using transfer learning. This implementation is advantageous for denoising ultra-high-resolution medical image data. With ultra-high-resolution comes a severe noise penalty. In these instances, natural images serve as a very high resolution and low noise signal that is advantageous for training. By implementing this natural image training variant performance on ultra-high resolution scan modes can be significantly improved. Additionally, this variant makes the phantom-based training framework even more widely accessible as it does not require subject medical image data for its implementation. For instance, because natural image databases are publically available for training, any institution can implement noise reduction with a single acquisition (e.g., a single phantom acquisition). Using a natural image database for training also provides a diverse feature space, which is advantageous for robust network performance.

Figure 5:
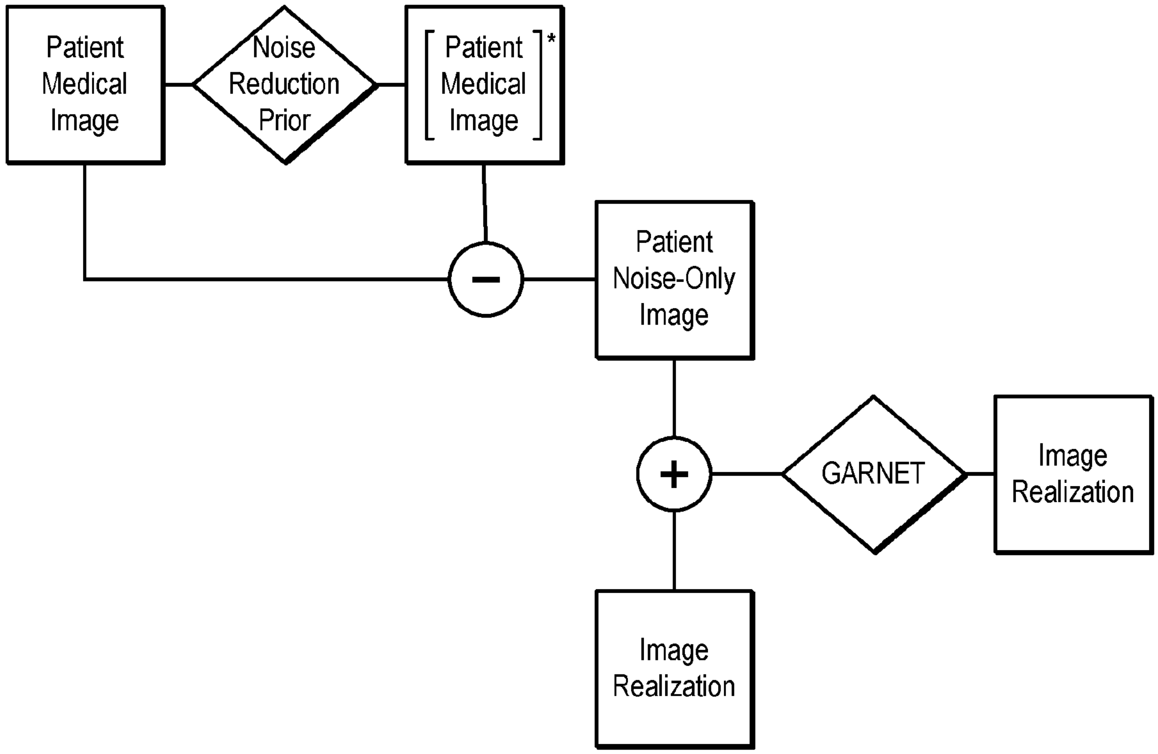
FIG. 5 illustrates an example workflow for generating noise-only images from previously acquired patient medical images.

Additionally or alternatively, noise-only images used for training can be generated using previously acquired patient images (this is in place of the phantom-based noise-only images used in the previously mentioned methods). Referring now to FIG. 5, patient noise-only images can be extracted by applying a noise reduction prior (e.g., CNN, GARNET-CNN, iterative reconstruction, or any other medical image noise reduction method) to patient medical images. The noise-only image refers to the noise and artifacts removed by the noise reduction prior method in these instances. These noise-only images can then be used for training in a similar way as the phantom noise patches (noise-only images superimposed on patient medical images; CNN trained to remove the noise-only images from patient data). This method can be used, advantageously, for patient-specific fine-tuning of the CNN.

Figure 6:
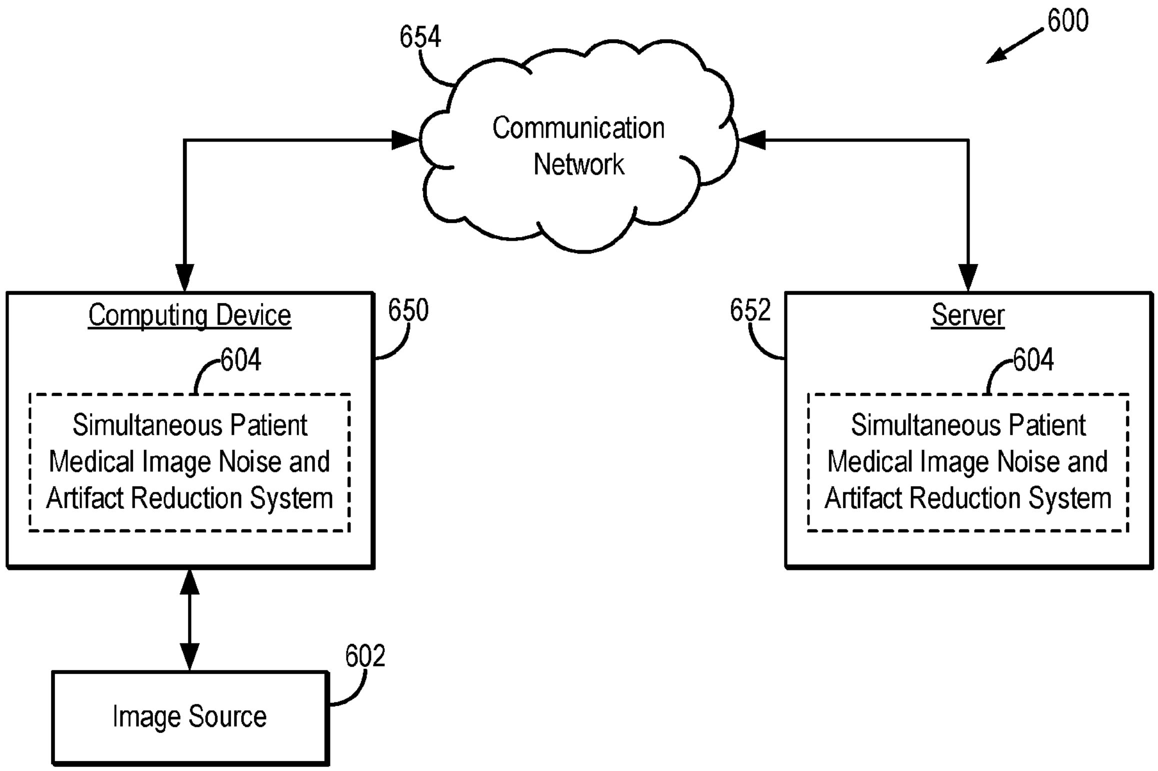
FIG. 6 is a block diagram of an example system that can be implemented for simultaneously reducing noise and artifacts in patient medical images.

Referring now to FIG. 6, an example of a system 600 for generating uncorrupted patient medical images, in which noise and artifacts have been removed or otherwise reduced, in accordance with some embodiments of the systems and methods described in the present disclosure is shown. As shown in FIG. 6, a computing device 650 can receive one or more types of data (e.g., noise and/or artifact corrupted patient medical image data) from image source 602, which may be a patient medical image source. In some embodiments, computing device 650 can execute at least a portion of a simultaneous patient medical image noise and artifact reduction system 604 to remove or otherwise reduce noise and artifacts from patient medical image data received from the image source 602.

Additionally or alternatively, in some embodiments, the computing device 650 can communicate information about data received from the image source 602 to a server 652 over a communication network 654, which can execute at least a portion of the simultaneous patient medical image noise and artifact reduction system 604. In such embodiments, the server 652 can return information to the computing device 650 (and/or any other suitable computing device) indicative of an output of the simultaneous patient medical image noise and artifact reduction system 604.

In some embodiments, computing device 650 and/or server 652 can be any suitable computing device or combination of devices, such as a desktop computer, a laptop computer, a smartphone, a tablet computer, a wearable computer, a server computer, a virtual machine being executed by a physical computing device, and so on. The computing device 650 and/or server 652 can also reconstruct images from the data.

In some embodiments, image source 602 can be any suitable source of image data (e.g., measurement data, images reconstructed from measurement data), such as a medical imaging system (e.g., a CT system, an MRI system, an ultrasound system, an optical imaging system), another computing device (e.g., a server storing image data), and so on. In some embodiments, image source 602 can be local to computing device 650. For example, image source 602 can be incorporated with computing device 650 (e.g., computing device 650 can be configured as part of a device for capturing, scanning, and/or storing images). As another example, image source 602 can be connected to computing device 650 by a cable, a direct wireless link, and so on. Additionally or alternatively, in some embodiments, image source 602 can be located locally and/or remotely from computing device 650, and can communicate data to computing device 650 (and/or server 652) via a communication network (e.g., communication network 654).

In some embodiments, communication network 654 can be any suitable communication network or combination of communication networks. For example, communication network 654 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 654 can be a local area network, a wide area network, a public network (e.g., the Internet), a private or semi-private network (e.g., a corporate or university intranet), any other suitable type of network, or any suitable combination of networks. Communications links shown in FIG. 6 can each be any suitable communications link or combination of communications links, such as wired links, fiber optic links, Wi-Fi links, Bluetooth links, cellular links, and so on.

Figure 7:
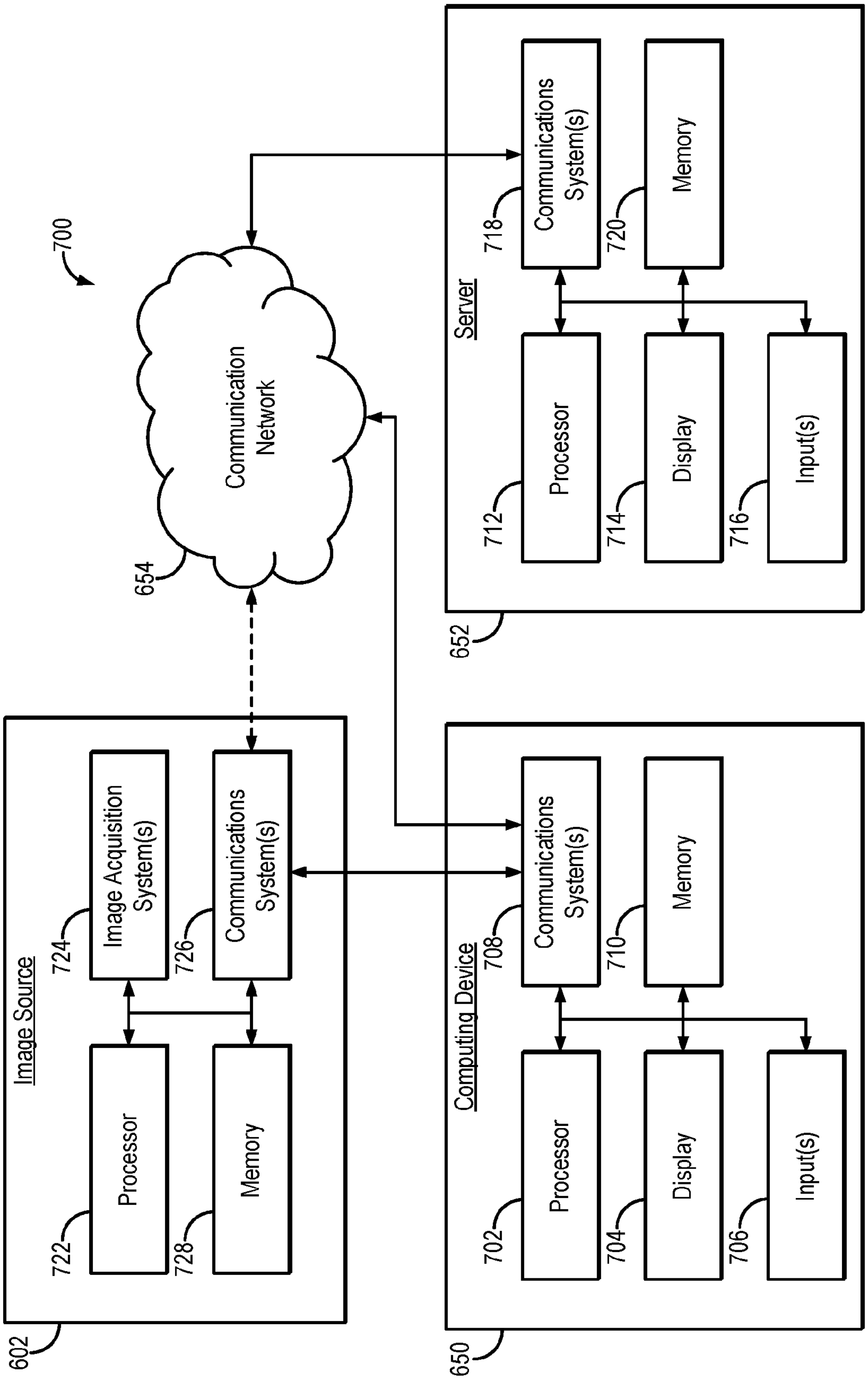
FIG. 7 is a block diagram of example components that can implement the system of FIG. 6.

Referring now to FIG. 7, an example of hardware 700 that can be used to implement image source 602, computing device 650, and server 652 in accordance with some embodiments of the systems and methods described in the present disclosure is shown. As shown in FIG. 7, in some embodiments, computing device 650 can include a processor 702, a display 704, one or more inputs 706, one or more communication systems 708, and/or memory 710. In some embodiments, processor 702 can be any suitable hardware processor or combination of processors, such as a central processing unit ("CPU"), a graphics processing unit ("GPU"), and so on. In some embodiments, display 704 can include any suitable display devices, such as a computer monitor, a touchscreen, a television, and so on. In some embodiments, inputs 706 can include any suitable input devices and/or sensors that can be used to receive user input, such as a keyboard, a mouse, a touchscreen, a microphone, and so on.

In some embodiments, communications systems 708 can include any suitable hardware, firmware, and/or software for communicating information over communication network 654 and/or any other suitable communication networks. For example, communications systems 708 can include one or more transceivers, one or more communication chips and/or chip sets, and so on. In a more particular example, communications systems 708 can include hardware, firmware and/or software that can be used to establish a Wi-Fi connection, a Bluetooth connection, a cellular connection, an Ethernet connection, and so on.

In some embodiments, memory 710 can include any suitable storage device or devices that can be used to store instructions, values, data, or the like, that can be used, for example, by processor 702 to present content using display 704, to communicate with server 652 via communications system(s) 708, and so on. Memory 710 can include any suitable volatile memory, non-volatile memory, storage, or any suitable combination thereof. For example, memory 710 can include RAM, ROM, EEPROM, one or more flash drives, one or more hard disks, one or more solid state drives, one or more optical drives, and so on. In some embodiments, memory 710 can have encoded thereon, or otherwise stored therein, a computer program for controlling operation of computing device 650. In such embodiments, processor 702 can execute at least a portion of the computer program to present content (e.g., images, user interfaces, graphics, tables), receive content from server 652, transmit information to server 652, and so on.

In some embodiments, server 652 can include a processor 712, a display 714, one or more inputs 716, one or more communications systems 718, and/or memory 720. In some embodiments, processor 712 can be any suitable hardware processor or combination of processors, such as a CPU, a GPU, and so on. In some embodiments, display 714 can include any suitable display devices, such as a computer monitor, a touchscreen, a television, and so on. In some embodiments, inputs 716 can include any suitable input devices and/or sensors that can be used to receive user input, such as a keyboard, a mouse, a touchscreen, a microphone, and so on.

In some embodiments, communications systems 718 can include any suitable hardware, firmware, and/or software for communicating information over communication network 654 and/or any other suitable communication networks. For example, communications systems 718 can include one or more transceivers, one or more communication chips and/or chip sets, and so on. In a more particular example, communications systems 718 can include hardware, firmware and/or software that can be used to establish a Wi-Fi connection, a Bluetooth connection, a cellular connection, an Ethernet connection, and so on.

In some embodiments, memory 720 can include any suitable storage device or devices that can be used to store instructions, values, data, or the like, that can be used, for example, by processor 712 to present content using display 714, to communicate with one or more computing devices 650, and so on. Memory 720 can include any suitable volatile memory, non-volatile memory, storage, or any suitable combination thereof. For example, memory 720 can include RAM, ROM, EEPROM, one or more flash drives, one or more hard disks, one or more solid state drives, one or more optical drives, and so on. In some embodiments, memory 720 can have encoded thereon a server program for controlling operation of server 652. In such embodiments, processor 712 can execute at least a portion of the server program to transmit information and/or content (e.g., data, images, a user interface) to one or more computing devices 650, receive information and/or content from one or more computing devices 650, receive instructions from one or more devices (e.g., a personal computer, a laptop computer, a tablet computer, a smartphone), and so on.

In some embodiments, image source 602 can include a processor 722, one or more image acquisition systems 724, one or more communications systems 726, and/or memory

728. In some embodiments, processor 722 can be any suitable hardware processor or combination of processors, such as a CPU, a GPU, and so on. In some embodiments, the one or more image acquisition systems 724 are generally configured to acquire data, images, or both, and can include a medical imaging system (e.g., a CT system, an MRI system, an ultrasound system, an optical imaging system). Additionally or alternatively, in some embodiments, one or more image acquisition systems 724 can include any suitable hardware, firmware, and/or software for coupling to and/or controlling operations of a medical imaging system. In some embodiments, one or more portions of the one or more image acquisition systems 724 can be removable and/or replaceable.

Note that, although not shown, image source 602 can include any suitable inputs and/or outputs. For example, image source 602 can include input devices and/or sensors that can be used to receive user input, such as a keyboard, a mouse, a touchscreen, a microphone, a trackpad, a trackball, and so on. As another example, image source 602 can include any suitable display devices, such as a computer monitor, a touchscreen, a television, etc., one or more speakers, and so on.

In some embodiments, communications systems 726 can include any suitable hardware, firmware, and/or software for communicating information to computing device 650 (and, in some embodiments, over communication network 654 and/or any other suitable communication networks). For example, communications systems 726 can include one or more transceivers, one or more communication chips and/or chip sets, and so on. In a more particular example, communications systems 726 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 728 can include any suitable storage device or devices that can be used to store instructions, values, data, or the like, that can be used, for example, by processor 722 to control the one or more image acquisition systems 724, and/or receive data from the one or more image acquisition systems 724; to images from data; present content (e.g., images, a user interface) using a display; communicate with one or more computing devices 650; and so on. Memory 728 can include any suitable volatile memory, non-volatile memory, storage, or any suitable combination thereof. For example, memory 728 can include RAM, ROM, EEPROM, one or more flash drives, one or more hard disks, one or more solid state drives, one or more optical drives, and so on. In some embodiments, memory 728 can have encoded thereon, or otherwise stored therein, a program for controlling operation of image source 602. In such embodiments, processor 722 can execute at least a portion of the program to generate images, transmit information and/or content (e.g., data, images) to one or more computing devices 650, receive information and/or content from one or more computing devices 650, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A method for reducing noise and artifacts in previously reconstructed medical images, the method comprising:

(a) accessing patient medical image data with a computer system, wherein the patient medical image data comprise one or more medical images acquired with a medical imaging system and depicting a patient;

(b) accessing a trained neural network with the computer system, wherein the trained neural network has been trained on training data comprising augmented image data and ground truth data, wherein the augmented image data comprise at least one of noise-augmented image data or artifact-augmented image data; and (c) inputting the patient medical image data to the trained neural network using the computer system, generating output as uncorrupted patient medical image data, wherein the uncorrupted patient medical image data comprise one or more medical images depicting the patient and having reduced noise and artifacts relative to the patient medical image data, wherein the noise-augmented image data are generated by combining image data with noise-only image data generated from medical image data acquired with the medical imaging system by separating noise and artifact image content of the medical image data from signal components of the medical image data.

2. The method of claim 1, wherein the image data comprise medical image data obtained with the medical imaging system.

3. The method of claim 1, wherein the image data comprise natural image data retrieved from a natural image database.

4. The method of claim 1, wherein the augmented image data comprise noise-augmented image data generated by adding the image data with the noise-only image data.

5. The method of claim 1, wherein the augmented image data comprise artifact-augmented image data generated by extracting artifacts from additional image data and adding the extracted artifacts with the image data.

6. The method of claim 5, wherein the additional image data comprise at least one of additional patient medical image data or natural image data retrieved from a natural image database.

7. The method of claim 1, wherein the augmented image data comprise both noise-augmented image data and artifact-augmented image data.

8. The method of claim 1, wherein the trained neural network comprises a convolutional neural network.

9. The method of claim 1, wherein the medical imaging system is at least one of an x-ray imaging system, a computed tomography (CT) system, a magnetic resonance imaging (MRI) system, an ultrasound system, or an optical imaging system.

10. The method of claim 1, wherein the noise-only image data are generated from at least one of phantom image data acquired with the medical imaging system or additional patient image data acquired with the medical imaging system.

11. The method of claim 10, wherein the additional patient image data are acquired from the patient using the medical imaging system.

12. The method of claim 3, wherein the natural image database is an ImageNet database.

* * * * *